United States Patent
Böhm et al.

(10) Patent No.: US 8,249,355 B2
(45) Date of Patent: Aug. 21, 2012

(54) METHOD AND DEVICE FOR NOISE SUPPRESSION IN MEDICAL IMAGES

(75) Inventors: Stefan Böhm, Oberasbach (DE); Sandra Martin, Herzogenaurauch (DE)

(73) Assignee: Siemens Aktiengesellschaft, München (DE)

(*) Notice: Subject to any disclaimer, the term of this patent is extended or adjusted under 35 U.S.C. 154(b) by 943 days.

(21) Appl. No.: 12/313,566

(22) Filed: Nov. 21, 2008

(65) Prior Publication Data
US 2009/0148015 A1    Jun. 11, 2009

(30) Foreign Application Priority Data
Dec. 5, 2007    (DE) .................. 10 2007 058 498

(51) Int. Cl.
G06K 9/40    (2006.01)
G06T 5/00    (2006.01)

(52) U.S. Cl. ................... 382/199; 382/261; 382/275

(58) Field of Classification Search .......... 382/199, 382/260, 261, 275
See application file for complete search history.

(56) References Cited

U.S. PATENT DOCUMENTS

| | | | |
|---|---|---|---|
| 5,343,309 A | 8/1994 | Roetling | |
| 5,819,035 A * | 10/1998 | Devaney et al. | 709/202 |
| 2006/0020203 A1* | 1/2006 | Tamura | 600/437 |
| 2006/0039590 A1* | 2/2006 | Lachine et al. | 382/128 |
| 2008/0199101 A1* | 8/2008 | Sumiya et al. | 382/266 |

FOREIGN PATENT DOCUMENTS

| | | |
|---|---|---|
| DE | 10309166 A1 | 9/2004 |
| EP | 1434424 A2 | 6/2004 |

OTHER PUBLICATIONS

Carrato et al. "A Gradient-Directed Adaptive Algorithm for Synchrotron Radiation Angiography." Proceedings, 6th Mediterranean Electrotechnical Confererence, vol. 1, May 22, 1991, pp. 759-762.*

Jha et al. "Edge Adaptive Filtering: How Much and Which Direction?" Proceedings, IEEE International Conference on Systems, Man and Cybernetics, vol. 1, 1989, pp. 364-366.*

Teramoto et al. "Improvement of Image Quality in MR Image Using Adaptive K-nearest Neighbor Averaging Filter." Proceedings, International Conference on Information, Communications and Signal Processing, vol. 1, Sep. 9, 1997, pp. 190-194.*

* cited by examiner

Primary Examiner — Jon Chang

(57) ABSTRACT

The invention relates to a method for noise suppression in medical images comprising steps of measuring the gradient field strength of an image pixel and selecting a suitable filter mask for noise suppression as a function of the gradient field strength, with the value of the gradient field strength being compared with a predetermined threshold value. The method is repeated when an additional image pixel is selected. A decision is made per read-in image pixel as to which type of filter mask is used for filtering. A selection can be made between filter masks of different sizes or isotropic or anisotropic or directional filter masks. The decision is based on the measured gradient field strength of the respective pixel. The use of different filter masks allows the signal-to-noise ratio to be improved, without distorting structures like edges for instance and without generating artificial structures in homogenous noise regions.

13 Claims, 4 Drawing Sheets

| 0° | | | | 45° | | | | 90° | | | | 135° | | |
|---|---|---|---|---|---|---|---|---|---|---|---|---|---|---|
| 1 | 2 | 1 | | 2 | 1 | 0 | | 1 | 0 | 1 | | 0 | 1 | 2 |
| 0 | 0 | 0 | | 1 | 0 | 1 | | 2 | 0 | 2 | | 1 | 0 | 1 |
| 1 | 2 | 1 | | 0 | 1 | 2 | | 1 | 0 | 1 | | 2 | 1 | 0 |

$$\text{gradient} = g_{0°}^2 + g_{45°}^2 + g_{90°}^2 + g_{135°}^2$$

18  19  20  21  22  23  24  25

METHOD AND DEVICE FOR NOISE SUPPRESSION IN MEDICAL IMAGES

CROSS REFERENCE TO RELATED APPLICATIONS

This application claims priority of German application No. 10 2007 058 498.0 filed Dec. 5, 2007, which is incorporated by reference herein in its entirety.

FIELD OF THE INVENTION

The invention relates to a method and a device for noise suppression in medical images, in particular for use in an x-ray diagnostic device.

BACKGROUND OF THE INVENTION

The lowest dose is usually used in order to create fluoroscopic x-ray images during navigation using the guide wire and the catheter and/or during the use of a stent as well as during vascular imaging. This low dose results in a very low signal-to-noise ratio so that the image quality is extremely restricted.

To improve the image quality, temporal and/or local filterings are implemented. The temporal filtering is disadvantageous in that movement blurrings and double images appear. The local low pass filtering is known as an alternative here, in which a distortion of the objects, for instance the vessel edges, is to be accepted.

DE 103 09 166 A1 discloses an x-ray diagnostic device, which has a device for detecting edges in x-ray images and a device for filtering the individual x-ray images along these edges. Here the direction of the filtering is determined, with the used filter mask remaining fixed. One disadvantage of this directional filtering consists in artificial structures, e.g. so-called swirls and/or worm threads possibly developing in homogenous noise regions. Such filters can thus only be used in restricted filter strengths.

SUMMARY OF THE INVENTION

The object underlying the invention is to develop a method and/or a device of the type mentioned in the introduction such that the signal to noise ratio of real-time images and/or image series is improved without generating artificial structures in noise regions.

This object is achieved by the features specified in the independent claims. Advantageous developments of the invention are specified in the dependent claims.

One aspect of the invention is a method for noise suppression in medical images, comprising the following steps:
a) measuring the gradient field strength of an image pixel,
b) selecting a suitable filter mask for noise suppression as a function of the gradient strength measured under a), with the value of the gradient field strength being compared with at least one predetermined threshold value.

This method can be repeated when selecting a further image pixel.

In other words, a decision is made per read-in image pixel as to which type of filter mask is used for filtering purposes. It is possible to choose between filter masks of different sizes and/or between isotropic and anisotropic and/or directional filter masks. The decision is based on the measured gradient field strength of the respective pixel. Here the size of the filter mask can be determined on the basis of the measured gradient field strength.

The signal-to-noise ratio can be improved by using different filter masks without distorting structures like edges for instance and without generating artificial structures in homogenous noise regions.

One further aspect of the invention is an image system and/or device as well as a computer program product and a storage medium, which are embodied with means and/or modules such that the afore-cited inventive method can be implemented.

Further embodiments of the invention and their advantages result from the exemplary embodiments described below.

BRIEF DESCRIPTION OF THE DRAWINGS

The invention is described in more detail below with reference to exemplary embodiments illustrated in the drawing, in which.

DETAILED DESCRIPTION OF THE INVENTION

Figure 1:
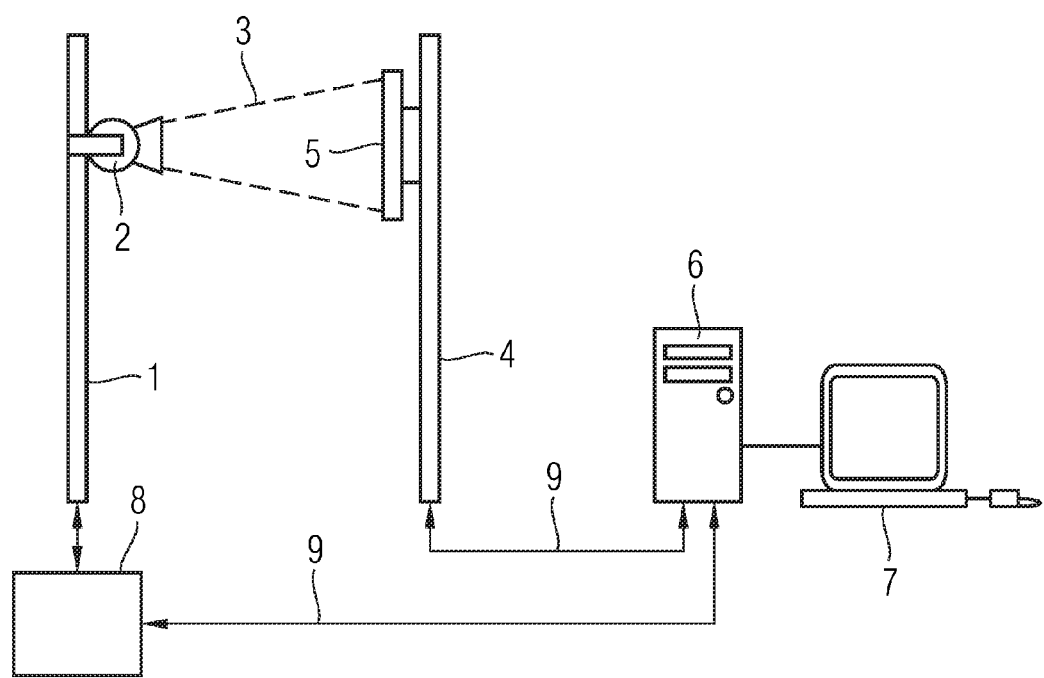
FIG. 1 shows a known x-ray diagnostic device.

FIG. 1 shows an x-ray diagnostic device known from DE 103 09 166 A1 with a first stand 1, to which an x-ray emitter 2 is attached in a height-adjustable fashion, which generates a conical x-ray beam 3 and a second stand 4, to which an x-ray detector 5 is fastened such that it is aligned to the x-ray emitter 2 in respect of its height and that the x-ray radiation 3 strikes the x-ray detector 5. The output signal of the x-ray detector 5 is fed to an image computer or image system 6. The image system 6 can have a computer, converter, image memory and processing circuits. It is connected to a playback device, e.g. a control monitor 7, in order to play back the detected x-ray images. A high voltage generator 8 supplies the x-ray tubes of the x-ray emitter 2 with high voltage and heating voltage. The image system 6 is connected to the remaining components of the x-ray diagnostic device by way of control and data lines 9.

Figure 2:
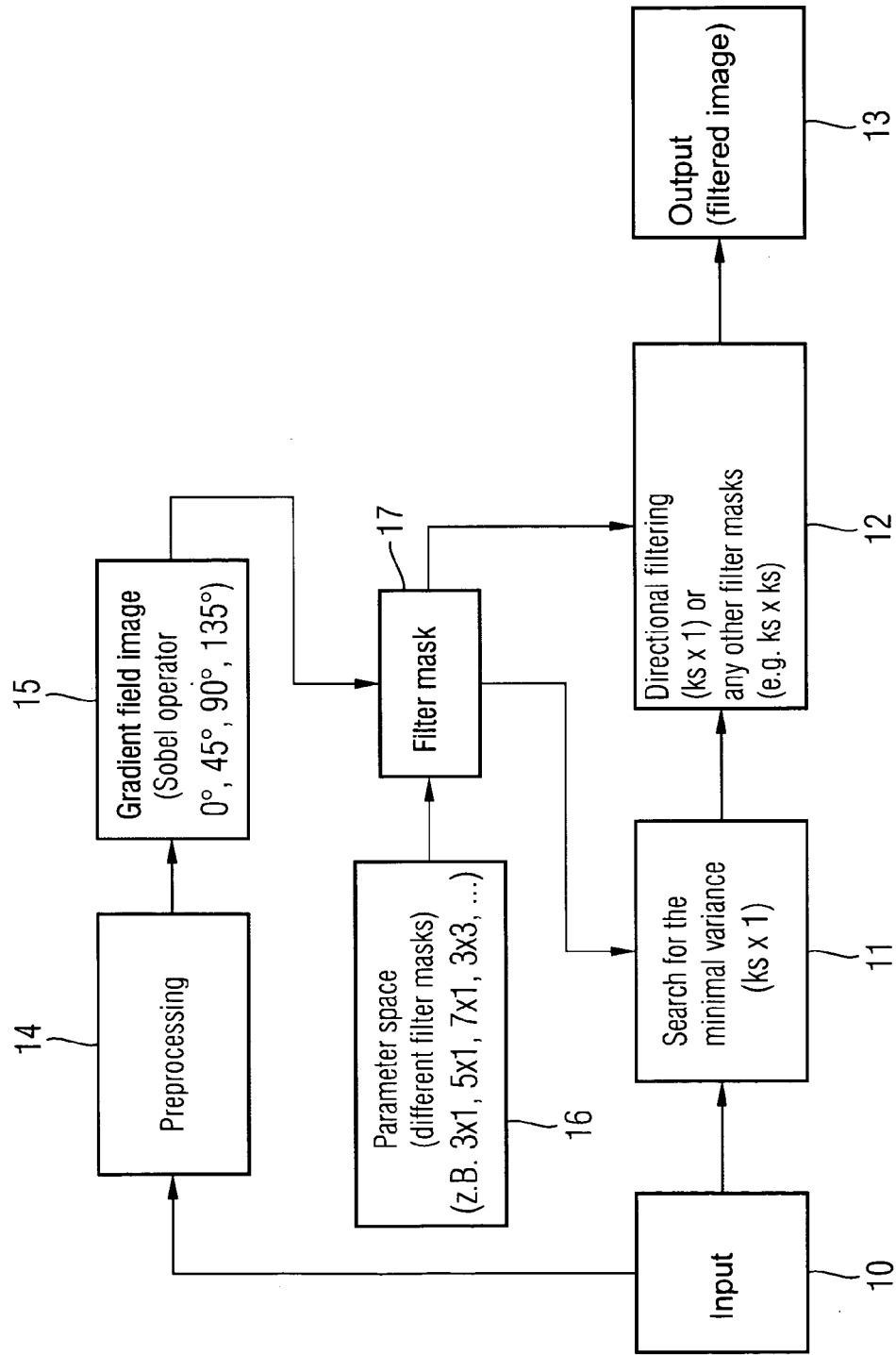
FIG. 2 shows a schematic representation of the inventive procedure.

The image system 6 of the x-ray diagnostic device according to FIG. 1 has means for implementing the method according to the invention, which is described in more detail in FIG. 2.

An input signal is fed to the input 10, the output signal of which strikes a variance measurement in order to determine the minimum of the variances with means 11. The result of the minimum determination influences the type of filtering, in particular the directional filtering, which is implemented by device 12. A filtered image and/or a filtered image series develops at the output 13 as a result of this filtering which is implemented per image pixel.

For an example with nine image pixels in the filter mask according to the following formula for pixel values $p_i$, the means 11 for variance measurement and determination of the minimal variance calculate the average value $\bar{p}$ of the pixel values, which is subtracted from the pixel value $p_i$ (marked as dark in FIG. 4 in each instance), square the result and form therefrom the average value:

$$\text{Var} = \sum_{i=0}^{8} (p_i - \overline{p})^2 / 9$$

The variance measurement is carried out in a directional-dependent fashion, i.e. within the filter mask.

The minimum is determined for these variances so that the direction of edges results herefrom. This result is fed to the device 12 for filtering purposes, by means of which a filtering takes place along the edges by means of average determination of a directional filter mask shown in FIG. 4.

Figures 3, 4:
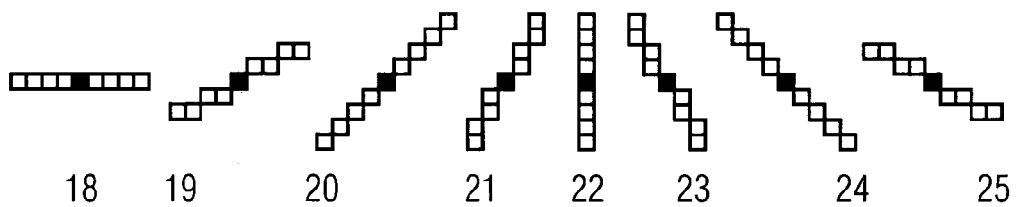
FIG. 3 shows an example of determining the gradient field strength.
FIG. 4 shows a variance measurement in the case of a directional mask.

FIG. 4 shows examples of directional fields 18 to 25 of the filter masks for eight different directions. Other and more different directions as well as higher numbers of pixels to be averaged are however also still possible.

A preprocessing, like for instance the reading-in and/or scanning of an image pixel of a recorded x-ray image and/or image series is also initiated from the input 10 by means of a signal with means 14. Here an image pixel is scanned one by one e.g. line by line and/or column by column. Furthermore, the gradient field strength of the scanned image pixel is measured, which can be represented and/or expressed for instance by means 15 for determining a gradient field image by means of the so-called Sobel operator, Roberts operator, Laplace filter, Prewitt operator, Kirsch operator, Kompass operator, Canny operator and/or Robinson operator for instance. In the example, the so-called Sobel-Operator is used for gradient field determination—as shown in FIG. 3.

A filter mask 17 is determined using means 16 for selecting a filter mask as a function of the measured gradient field strength on the basis of the means 15, said filter mask 17 being considered during the variance minimum determination (means 11) and being used for filtering purposes (device 12). Instead of the variance measurement and minimum determination, other methods could also be used for directional determination and subsequent smoothing.

Figure 5:
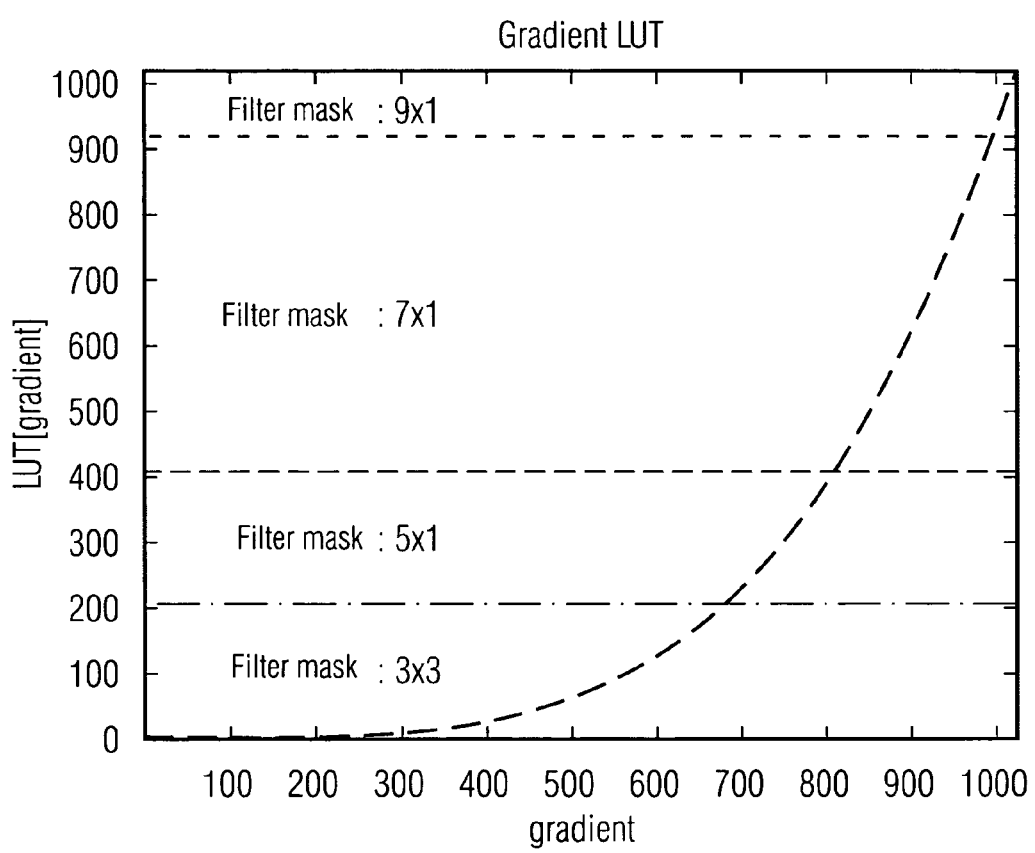
FIG. 5 shows an example of a characteristic curve for adjusting the gradient field strength.

The filter mask 17 can be configured in the form of an isotropic, anisotropic and/or directional filter mask for instance. The size of the useable filter masks is determined by a parameter space e.g. 3×1, 5×1, 7×1, 3×3-mask, which is selected as a function of the gradient field image. Here, different threshold values, as shown in FIG. 5 for instance, can be predetermined. FIG. 5 shows a division of the gradient field strength into four regions, to which a size of the filter mask 3×3 and/or 5×1 and/or 7×1 and/or 9×1 is assigned in each instance. When a predetermined threshold value like for instance according to FIG. 5, Gradient LUT (Look Up Table) a threshold value of 200 is not reached, a 3×3 filter mask and/or an isotropic filter mask is selected for instance. If the predetermined threshold value is exceeded, a 5×1 and/or an anisotropic and/or directional filter mask is selected for instance. The measured gradient field strength with a suitable characteristic curve, which is shown in FIG. 5 as a slightly bent dashed line, can be adjusted to the respective use as a function of the desired filter effect. The input for the characteristic curve is the calculated gradient field strength (per pixel). In the example, small gradient field strengths are compressed and large gradient field strengths are extended. As a result, the signal-to-disturbance ratio of the gradient field image is improved.

Depending on the selected filter form and/or filter size (kernel characteristic and/or size), image quality-relevant influence variables like the filter strength (fading factor for the original, weighting of the gradient field image) can also be adjusted to a user interface.

The described method and/or device can also be implemented on a digital signal processor (DSP) as software and/or as a computer program product, which can be stored on a storage medium (e.g. DVD) such that it enables the real-time image processing and can be used in a image system (e.g. image system 6 in FIG. 1).

The invention claimed is:

1. A method for suppressing a noise in a medical image, comprising:
    measuring a gradient field strength of an image pixel of the medical image;
    selecting a filter mask for filtering the noise as a function of the measured gradient field strength;
    comparing the measured gradient field strength with a predetermined threshold value;
    measuring a variance of the gradient field strength,
    determining a minimum variance of the measured variance, and
    determining an optimum direction of the filtering based on the minimum variance.

2. The method as claimed in claim 1, wherein the steps of measuring, selecting, and comparing are repeated for an additional image pixel of the medical image.

3. The method as claimed in claim 1, wherein a type of the filter mask is selected based on the measured gradient field strength.

4. The method as claimed in claim 1, wherein a size of the filter mask is selected based on the measured gradient field strength.

5. The method as claimed in claim 1, wherein a size of the filter mask is increased with the measured gradient field strength.

6. The method as claimed in claim 1, wherein an anisotropic filter mask is selected if the measured gradient field strength exceeds the predetermined threshold value.

7. The method as claimed in claim 1, wherein a directional filter mask is selected if the measured gradient field strength exceeds the predetermined threshold value.

8. The method as claimed in claim 1, wherein an isotropic filter mask is selected if the measured gradient field strength does not exceed the predetermined threshold value.

9. The method as claimed in claim 1, wherein a strength of the filtering is adjusted depending on the filter mask being selected.

10. The method as claimed in claim 1, wherein the measured gradient field strength is adjusted by a characteristic curve.

11. An image system for recording a medical image, comprising:
    a measuring device for measuring a gradient field strength of an image pixel of the medical image;
    a selecting device for selecting a filter mask for filtering the noise as a function of the measured gradient field strength; and
    a comparing device for comparing the measured gradient field strength with a predetermined threshold value,
    wherein the measuring device further:
        measuring a variance of the gradient field strength,
        determining a minimum variance of the measured variance, and
        determining an optimum direction of the filtering based on the minimum variance.

12. The image system as claimed in claim 11, wherein the medical image is an x-ray image.

13. A storage device used on a computer, wherein a computer program is stored on or in the storage device for suppressing a noise in a medical image executing the steps of:

measuring a gradient field strength of an image pixel of the medical image;

selecting a filter mask for filtering the noise as a function of the measured gradient field strength;

comparing the measured gradient field strength with a predetermined threshold value;

measuring a variance of the gradient field strength, determining a minimum variance of the measured variance, and determining an optimum direction of the filtering based on the minimum variance.

\* \* \* \* \*